(12) United States Patent
Heuer et al.

(10) Patent No.: US 7,374,785 B1
(45) Date of Patent: May 20, 2008

(54) COMPOSITION FOR A FEELING OF CALMNESS

(75) Inventors: Marvin Heuer, Mississauga (CA); Ken Clement, Mississauga (CA); Shan Chaudhuri, Mississauga (CA); Megan Thomas, Mississauga (CA)

(73) Assignee: Iomedix Development International SRL, Belleville, St. Michael (BB)

( * ) Notice: Subject to any disclaimer, the term of this patent is extended or adjusted under 35 U.S.C. 154(b) by 0 days.

(21) Appl. No.: 11/696,945

(22) Filed: Apr. 5, 2007

(51) Int. Cl.
*A01N 65/00* (2006.01)

(52) U.S. Cl. .................................... 424/725

(58) Field of Classification Search ............... None
See application file for complete search history.

(56) References Cited

FOREIGN PATENT DOCUMENTS

| | | | |
|---|---|---|---|
| JP | 2003183135 | * | 7/2003 |
| SU | 946544 | * | 7/1982 |

OTHER PUBLICATIONS

Stoller MK. Economic effects of insomnia. Clin Ther. Sep.-Oct. 1994;16 (5):873-97.
Irwin M, et al. Partial night sleep deprivation reduces natural killer and cellular immune responses in humans. FASEB J. Apr. 1996;10(5):643-53.
Zanoli P, et al. New insight in the neuropharmacological activity of Humulus Iupulus L. J Ethnopharmacol. Oct. 31, 2005;102(1):102-6.
Schiller H, et al. Related Sedating effects of Humulus Iupulus L. extracts. Phytomedicine. Sep. 2006;13(8):535-41.
Aoshima H, et al. Effect of beer and hop on ionotropic gamma-aminobutyric acid receptors. J Argc Food Chem. Apr. 5, 2006;54(7):2514-9.
Thakur VD, et al. Neuropharmacological profile of Eclipta alba (Linn.) Hassk. J Ehtnopharmacol. Oct. 31, 2005;102(1):23-31 (Abstract).
Sawant M, et al. Analgesic studies on total alkaloids and alcohol extract of Eclipta alba (Linn.) Hassk. Phytother Res. Feb. 2004;18(2):111-3 (Abstract).
Joshi H, et al. Nardostachys jatamansi improves learning and memory in mice. J Med Food. 2006 Spring;9(1):113-8.
Prabhu V, et al. Effects of Nardostachys jatamansi on biogenic amines and inhibitory amino acids in the rat brain. Planta Med. Apr. 1994;60(2):114-7 (Abstract).
Farag NH and Mills PJ, A randomized-controlled trial of the effects of a traditional herbal supplement on sleep onset insomnia. Complementary Therapies in Medicine 2003, 11:223-225.
Morin Cm et al., Valerian hops combination and diphenhydramine for treating insomnia: a randomized placebo-controlled clinical trial. SLEEP 2005, 28:1465-1471.
International Search Report PCT/CA2007/00577, International filling date: April 5, 2007, Applicant: Iomedix Development International SRL et al.

* cited by examiner

*Primary Examiner*—Michael Meller
(74) *Attorney, Agent, or Firm*—Torys LLP

(57) ABSTRACT

A method for promoting restful, quality sleep in an individual comprising the administration of a composition comprising Hops extract, *Eclipta alba* extract powder, and *Nardostachys jatamansi* extract.

6 Claims, No Drawings

COMPOSITION FOR A FEELING OF CALMNESS

FIELD OF THE INVENTION

The present invention is directed towards supplemental compositions and methods for promoting restful sleep in an individual by producing a feeling of calmness.

BACKGROUND OF THE INVENTION

Sleep occupies about one-third of our life and is necessary for mental and physical well-being. It additionally affects mood, behavior and physiology. Sleep and the control of sleep is a complex process involving multiple neuro-chemical pathways and associated brain structures. It is a dynamic process involving a shift in the balance of distinct physiological changes, involving both positive and negative signaling neural signaling. The regulation of sleep in humans is governed by three processes—each influenced by hormonal and environmental factors: a daily sleep-wake cycle influenced by a circadian rhythm (24 hour cycle) tied to light-dark cycles.

The need for sleep is a biological drive similar to thirst or hunger. Interestingly though, the function of sleep is largely unknown, however some evidence indicates that sleep is required for learning. In North America, insomnia is estimated to affect a significant portion of the population every year and is associated with health problems and concomitant economic losses to society (Stoller M K. Economic effects of insomnia. Clin Ther. 1994 Sep-Oct;16(5):873-97 Abstract). It is clear that the impairment of sleep is detrimental to one's health. In humans, mild sleep deprivation results in indications of impaired immune system function (Irwin M, McClintick J, Costlow C, Fortner M, White J, Gillin J C. Partial night sleep deprivation reduces natural killer and cellular immune responses in humans. FASEB J. 1996 April; 10(5):643-53). Prolonged sleep deprivation is even known to result in death. It has been determined by many that an individual can survive longer without food than one can without sleep; thus indicating the importance of sleep.

Strategies to improve sleep are beneficial, not only in terms of one's physical health, but also in terms of emotional health. Furthermore, reinforcement of sleep of adequate quantity and quality positively impacts most aspect of daily life.

SUMMARY OF THE INVENTION

The foregoing needs and other needs and objectives that will become apparent for the following description are achieved in the present invention, which comprises an extract of Hops, Eclipta alba powder, and *Nardostachys jatamansi* for the promotion of restful sleep in an individual by producing a feeling of calmness.

DETAILED DESCRIPTION OF THE INVENTION

In the following description, for the purposes of explanations, numerous specific details are set forth in order to provide a thorough understanding of the present invention. It will be apparent, however, to one of ordinary skill in the art that the present invention may be practiced without these specific details.

The present invention is directed towards a composition for promoting feeling of calmness in an individual comprising and extract of Hops, *Eclipta alba* powder, and *Nardostachys jatamansi*. A method for promoting a restful period of sleep via an induction of a calming feeling in an individual is also provided comprising the step of administration of, to an individual, a composition comprising Hops, *Eclipta alba* powder, and *Nardostachys jatamansi* to produce a feeling of calmness.

Incorporated herein by reference are the specifications of co-pending applications (filed contemporaneously with the present application) entitled "Composition for a Feeling of Relaxation" and "Composition for Supporting Restful Sleep".

The term 'sleep' for the purposes of the present invention is defined as a natural or artificially induced state of suspension of sensory and motor activity in an individual.

It is herein understood that improvements in sleep may be both of a quantitative nature e.g. an increase in the length of sleep, a decreased in the time of sleep onset, and of a qualitative nature e.g. a deeper, more restful undisturbed period of sleep. It is further understood that improvements in sleep may also be both direct and indirect. For example, sleep will be directly improved by the administration of a substance which is known to reduce the time to sleep onset. Sleep may be indirectly improved, for example, by the administration of a substance which is known to result in feelings of relaxation and calmness. It is an aspect of the present invention to provide an individual consuming a composition of the present invention herein disclosed with an induced feeling of calmness, thus leading to improved sleep.

Hops (*Humulus lupulus*)

The Hop plant (*Humulus lupulus*) is a flowering vine used traditionally as a sedative for anxiety and sleep difficulties. In mice, Hops extract has been shown to have sleep-enhancing and antidepressant activities (Zanoli P, Rivasi M, Zavatti M, Brusiani F, Baraldi M. New insight in the neuropharmacological activity of *Humulus lupulus* L. J. Ethnopharmacol. 2005 Oct. 31; 102(1):102-6). Additionally, in rats, administration of Hops extract has been shown to produce sedative effects (Schiller H, Forster A, Vonhoff C, Hegger M, Biller A, Winterhoff H. Related Sedating effects of *Humulus lupulus* L. extracts. Phytomedicine. 2006 September; 13(8):535-41 Abstract). Hops extract has been shown to modulate the gamma-aminobutyric acid receptor (GABA(A) receptors) and display GABA-like activity (Aoshima H, Takeda K, Okita Y, Hossain S J, Koda H, Kiso Y. Effects of beer and hop on ionotropic gamma-aminobutyric acid receptors. J Agric Food Chem. 2006 Apr. 5; 54(7):2514-9); the mechanism at least in part responsible for the aforementioned effects. GABA is an inhibitory neurotransmitter that can induce relaxation and sleep. Modulation of any or all of these receptors may mediate the sleep-inducing activity of Hops.

In an embodiment of the present invention which is set forth in greater detail in the example below, the composition comprises an extract of Hops to promote a feeling of calmness and sedation through modulation of GABA-signaling. A serving of the supplemental composition comprises from about 0.001 g to about 0.500 g of an extract of Hops. The preferred dosage of an extract of Hops in the present invention comprises about 0.120 g. per serving.

*Eclipta alba*

The *Eclipta alba* plant grows as a weed in Asia and South America. It has been used in traditional medicine for many treatments. *Eclipta alba* extract has been shown to possess nootropic effects and attenuate stress-induced neurochemical changes in animal studies (Thakur V D, Mengi S A. Neuropharmacological profile of Eclipta alba (Linn.) Hassk. J. Ethnopharmacol. 2005 Oct 31; 102(1):23-31 Abstract) as well as have analgesic effects (Sawant M, Isaac J C, Narayanan S. Analgesic studies on total alkaloids and alcohol extracts of *Eclipta alba* (Linn.) Hassk. Phytother Res. 2004 February; 18(2):111-3 Abstract).

In an embodiment of the present invention which is set forth in greater detail in the example below, the composition comprises *Eclipta alba* powder to reduce the effects of stress conducive to a feeling of calmness. A serving of the supplemental composition comprises from about 0.001 g to about 0.100 g of *Eclipta alba* powder. The preferred dosage of *Eclipta alba* powder in the present invention comprises about 0.005 g per serving.

*Nardostachys jatamansi*

*Nardostachys jatamansi* herb is part of traditional Indian medicine where it is used for treatments affecting the central nervous system, particularly for depressant action (Joshi H, Parle M. *Nardostachys jatamansi* improves learning and memory in mice. J Med Food. 2006 Spring; 9(1):113-8). The effect of acute and subchronic administration of an extract of the roots of *Nardostachys jatamansi* has been shown to significantly increase serotonin (5-HT) in Wistar rats. In these experiments, however the levels of other neurochemicals such as norepinephrine and dopamine remained unchanged (Prabhu V, Karanth K S, Rao A Effects of *Nardostachys jatamansi* on biogenic amines and inhibitory amino acids in the rat brain. *Planta Med.* 1994 April; 60(2):114-7 (Abstract)). Serotonin is a neurochemical, concentrated in the raphe nucleus region of the brain wherein its axon project into several areas of the brain such as the hypothalamus. Through its resultant actions on the hypothalamus, serotonin is understood to be involved in inducing sleep and control of mood, among other function. In fact, many well-known antidepressants act by inducing serotonin release or inhibiting its re-uptake in the brains. It is herein understood by the inventors that increasing the amount of serotonin is beneficial to induce sleep and promote a feeling of calmness in an individual.

In an embodiment of the present invention which is set forth in greater detail in the example below, the composition comprises *Nardostachys jatamansi* to aid in promoting a feeling of calmness, an good mood and induce sleep in an individual following administration. A serving of the supplemental composition comprises from about 0.001 g to about 0.100 g of *Nardostachys jatamansi* extract. The preferred dosage of Nardostachys jatamansi extract in the present invention comprises about 0.020 g per serving.

In a preferred embodiment of the present invention, the composition comprises an extract of Hops, *Eclipta alba* powder, and *Nardostachys jatamansi* for the promotion of a restful period of sleep in an individual by producing a feeling of calmness.

Not wishing to be bound by theory, it is believed that the components of the present invention will act in concert through distinct mechanisms to promote a restful period of sleep by producing a feeling of calmness which will be conducive to the onset of sleep.

According to various embodiments of the present invention, the nutritional supplement may be consumed in any form. For instance, the dosage form of the nutritional supplement may be provided as, e.g., a powder beverage mix, a liquid beverage, a ready-to-eat bar or drink product, a capsule, a liquid capsule, a tablet, a caplet, or as a dietary gel. The preferred dosage forms of the present invention are as a tablet or caplet.

In an embodiment of the present invention the composition may be provided in a solid dosage form with specific controlled release characteristics. Advantageously, the composition may be provided in a layered solid dosage form. In such a form each individual layer will provide unique dissolution characteristics. In this way a controlled release of the composition can be achieved. In one aspect of this embodiment, each layer may contain a homogeneous mixture of ingredients whereby the release of the ingredients is dependent upon the characteristics of layer to which the ingredients are included. In an alternative aspect of this embodiment, each layer may contain a distinct set of specific ingredients which differ according to the layer such that different specific ingredients are released at different times. In all aspects of this embodiment, a temporally controlled release of ingredients is achieved.

Furthermore, the dosage form of the nutritional supplement may be provided in accordance with customary processing techniques for herbal and nutritional supplements in any of the forms mentioned above. Additionally, the nutritional supplement set forth in the example embodiment herein may contain any appropriate number and type of excipients, as is well known in the art.

The present nutritional composition or those similarly envisioned by one of skill in the art may be utilized in methods to promote and support a restful period of sleep in an individual. By way of ingestion of the composition of the present invention, a method for the promotion of restful sleep in an individual through inducing a feeling of calmness in an individual is provided. The method of the present invention comprises at least the step of administering to an individual a therapeutically acceptable amount of the composition of the present invention.

Advantageously, the present composition may be used not only as a sole means of promoting and supporting restful sleep but may also be used either in addition to other similarly-directed compositions or as a component of a larger composition.

Although the following example illustrates the practice of the present invention in one of its embodiments, the example should not be construed as limiting the scope of the invention. Other embodiments will be apparent to one of skill in the art from consideration of the specifications and example.

EXAMPLE

A nutritional supplement to help promote restful, quality sleep for use immediately prior to bedtime is provided in the following the composition. A serving of the nutritional supplement as a caplet contains the following ingredients:

About 0.120 g of an extract of Hops, about 0.005 g of, about 0.005 g of *Eclipta alba* powder, and about 0.020 g of *Nardostachys jatamansi*.

EXTENSIONS AND ALTERNATIVES

In the foregoing specification, the invention has been described with a specific embodiment thereof, however, it will be evident that various modifications and changes may be made thereto without departing from the broader spirit and scope of the invention.

What is claimed:

1. A composition comprising an effective amount of an extract of Hops, an effective amount of *Eclipta alba* powder, and an effective amount of *Nardostachys jatamansi* wherein said composition is in a controlled release solid dosage form.

2. The composition of claim 1 wherein the composition is provided in a therapeutically effective amount to synergistically induce sedation in an individual upon administration to said individual.

3. The composition of claim 1 wherein the composition is provided in a therapeutically effective amount to synergistically induce a feeling of calm in an individual upon administration to said individual.

4. A method of promoting restful sleep in an individual comprising the step of administering to the individual the composition of claim 1.

5. The method of claim 4 wherein the administration of the composition is effective to synergistically induce sedation in said individual.

6. The method of claim 4 wherein the administration of the composition synergistically induces a feeling of calm in said individual.

\* \* \* \* \*